(12) United States Patent
Llinas-Brunet et al.

(10) Patent No.: US 7,091,184 B2
(45) Date of Patent: Aug. 15, 2006

(54) HEPATITIS C INHIBITOR TRI-PEPTIDES

(75) Inventors: Montse Llinas-Brunet, Laval (CA); Murray D. Bailey, Laval (CA); Elise Ghiro, Laval (CA)

(73) Assignee: Boehringer Ingelheim International GmbH, Ingelheim (DE)

( * ) Notice: Subject to any disclaimer, the term of this patent is extended or adjusted under 35 U.S.C. 154(b) by 274 days.

(21) Appl. No.: 10/353,563

(22) Filed: Jan. 29, 2003

(65) Prior Publication Data
US 2003/0186895 A1 Oct. 2, 2003

Related U.S. Application Data

(63) Continuation-in-part of application No. 10/320,979, filed on Dec. 17, 2002, now abandoned.

(51) Int. Cl.
*A61K 38/00* (2006.01)
*A61K 38/05* (2006.01)
*C07K 5/06* (2006.01)

(52) U.S. Cl. .................. 514/18; 514/312; 530/331; 546/153

(58) Field of Classification Search .............. 514/2, 514/9, 17, 25, 57, 58, 64, 314, 563; 530/317
See application file for complete search history.

(56) References Cited

U.S. PATENT DOCUMENTS

| 6,159,938 A | 12/2000 | Gyorkos et al. |
| 6,187,905 B1 | 2/2001 | Hurst et al. |
| 6,323,180 B1 | 11/2001 | Llinas-Brunet et al. |
| 2004/0147483 A1* | 7/2004 | Priestley ............ 514/64 |

FOREIGN PATENT DOCUMENTS

| GB | 2 337 262 A | 11/1999 |
| JP | 10-298151 | 11/1998 |
| JP | 11-35478 | 2/1999 |
| JP | 11-127861 | 5/1999 |
| JP | 11-137252 | 5/1999 |
| JP | 11-292840 | 10/1999 |
| JP | 2001-103993 | 4/2001 |
| WO | WO 97/43310 A1 | 11/1997 |
| WO | WO 98/17679 A1 | 4/1998 |
| WO | WO 98/22496 A2 | 5/1998 |
| WO | WO 98/46597 A1 | 10/1998 |
| WO | WO 98/46630 A1 | 10/1998 |
| WO | WO 99/07733 A2 | 2/1999 |
| WO | WO 99/07734 A2 | 2/1999 |
| WO | WO 99/38888 A2 | 8/1999 |
| WO | WO 99/50230 A1 | 10/1999 |
| WO | WO 99/64442 A1 | 12/1999 |
| WO | WO 00/09543 | * 2/2000 |
| WO | WO 00/09543 A2 | 2/2000 |
| WO | WO 00/09543 A3 | 2/2000 |
| WO | WO 00/09558 A1 | 2/2000 |
| WO | WO 00/31129 A1 | 2/2000 |
| WO | WO 00/20400 A1 | 4/2000 |
| WO | WO 00/59929 A1 | 10/2000 |
| WO | WO 01/02424 A2 | 1/2001 |
| WO | WO 01/07407 A1 | 2/2001 |
| WO | WO 01/16357 A2 | 3/2001 |
| WO | WO 01/32691 A1 | 5/2001 |
| WO | WO 01/40262 A1 | 6/2001 |
| WO | WO 01/58929 A1 | 8/2001 |
| WO | WO 01/64678 A2 | 9/2001 |
| WO | WO 01/74768 A2 | 10/2001 |
| WO | WO 01/77113 A2 | 10/2001 |
| WO | WO 01/81325 A2 | 11/2001 |
| WO | WO 02/08187 A1 | 1/2002 |

(Continued)

OTHER PUBLICATIONS

Sibal et al. 2001, ILAR Journal, vol. 42, No. 2, pp. 74-84.*

(Continued)

*Primary Examiner*—Bruce Campell
*Assistant Examiner*—B. Dell Chism
(74) *Attorney, Agent, or Firm*—Michael P. Morris; Philip I. Datlow; Mary-Ellen Devlin

(57) ABSTRACT

Compounds of formula (I):

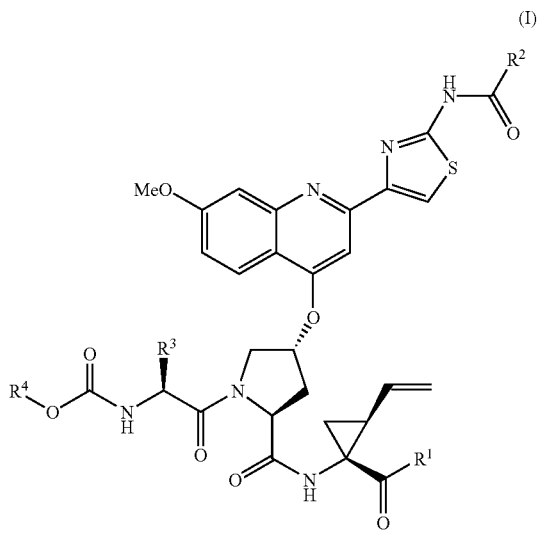

wherein $R^1$ is hydroxyl or sulfonamide derivative; $R^2$ is t-butyl or —$CH_2$—$C(CH_3)_3$ or —$CH_2$-cyclopentyl; $R^3$ is t-butyl or cyclohexyl and $R^4$ is cyclobutyl, cyclopentyl or cyclohexyl; or a pharmaceutically acceptable salt thereof, are described as useful as inhibitor of the HCV NS3 protease.

35 Claims, No Drawings

FOREIGN PATENT DOCUMENTS

| | | |
|---|---|---|
| WO | WO 02/08198 A2 | 1/2002 |
| WO | WO 02/08244 A2 | 1/2002 |
| WO | WO 02/08251 A2 | 1/2002 |
| WO | WO 02/08256 A2 | 1/2002 |
| WO | WO 02/18369 A2 | 3/2002 |
| WO | WO 02/060926 A2 | 8/2002 |
| WO | WO 02/079234 A1 | 10/2002 |

OTHER PUBLICATIONS

Huang, et al; "Olefin Metathesis-Active Ruthenium Complexes Bearing a Nucleophilic Carbene Ligand"; J. Am. Chem. Soc. 1999, 121, pp. 2674-2678.

Kingsbury, et al; "A Recyclable Ru-Based Metathesis Catalyst"; J. Am. Chem. Soc. 1999, 121, pp. 791-799.

Krchnak, et al; "Polymer-Supported Mitsunobu Ether Formation and its Use in Combinatorial Chemistry"; Tetrahedron Ltrs., vol. 36, No. 35, pp. 6193-6916, 1995.

Lohmann, et al; "Replication of Subgenomic Hepatitis C Virus RNAs in a Hepatoma Cell Line"; Science. 1999. vol. 285. pp. 110-113.

Miller, et al; "Application of Ring-Closing Metathesis to the Synthesis of Rigidified Amino Acids and Peptides"; J. Am. Chem. Soc. 1996, 118, pp. 9606-9614.

Mitsunobu; "The Use of Diethyl Azodicarboxylate and Triphenylphosphine in Synthesis and Transformation of Natural Products"; Synthesis (Reviews), pp. 1-28.

Rano, et al; "Solid Phase Synthesis of Aryl Ethers Via the Mitsunobu Reaction"; Tetrahedron Ltrs., 1995, vol. 36, No. 22, pp. 3789-3792.

Still, et al; "Rapid Chromatographic Technique for Preparative Separations with Moderate Resolution"; J. Org. Chem. 1978. vol. 43, No. 14, pp. 2923-2925.

Derwent Abstract: AN 2001-435746 [47] (JP2001103993).

Derwent Abstract: AN 1999-040664 [04] (JP 10298151).

Derwent Abstract: AN 1999-350322 [30] (JP 11127861).

Derwent Abstract: AN 2000-018687 [02] (JP 11292840).

Derwent Abstract AN 1999-186214 [16] (JP 11035478).

Derwent Abstract AN 1999-374374 [32] (JP 11137252).

* cited by examiner

SEQUENCE LISTING

<160> NUMBER OF SEQ ID NOS: 3

<210> SEQ ID NO 1
<211> LENGTH: 30
<212> TYPE: DNA
<213> ORGANISM: Artificial Sequence
<220> FEATURE:
<223> OTHER INFORMATION: Forward primer

<400> SEQUENCE: 1
acgcagaaag cgtctagcca tggcgttagt                                      30

<210> SEQ ID NO 2

```
<211> LENGTH: 30
<212> TYPE: DNA
<213> ORGANISM: Artificial Sequence
<220> FEATURE:
<223> OTHER INFORMATION: Reverse primer

<400> SEQUENCE: 2
tcccggggca ctcgcaagca ccctatcagg                                    30

<210> SEQ ID NO 3
<211> LENGTH: 26
<212> TYPE: DNA
<213> ORGANISM: Artificial Sequence
<220> FEATURE:
<223> OTHER INFORMATION: PUTR probe

<400> SEQUENCE: 3
tggtctgcgg aaccggtgag tacacc                                        26
```

HEPATITIS C INHIBITOR TRI-PEPTIDES

RELATED APPLICATIONS

This application is a Continuation-In-Part of U.S. Application Ser. No. 10/320,979, filed on Dec. 17, 2002 now abandoned, which application is herein incorporated by reference in its entirety.

FIELD OF THE INVENTION

The present invention relates to compounds, processes for their synthesis, compositions and methods for the treatment of hepatitis C virus (HCV) infection. In particular, the present invention provides novel peptide analogs, pharmaceutical compositions containing such analogs and methods for using these analogs in the treatment of HCV infection.

BACKGROUND OF THE INVENTION

Hepatitis C virus (HCV) is the major etiological agent of post-transfusion and community-acquired non-A non-B hepatitis worldwide. It is estimated that over 200 million people worldwide are infected by the virus. A high percentage of carriers become chronically infected and many progress to chronic liver disease, so-called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established. Immunoglobulins have been reported for prophylaxis of transfusion-associated viral hepatitis, however, the Center for Disease Control does not presently recommend immunoglobulins treatment for this purpose. The lack of an effective protective immune response is hampering the development of a vaccine or adequate post-exposure prophylaxis measures, so in the near-term, hopes are firmly pinned on antiviral interventions.

Various clinical studies have been conducted with the goal of identifying pharmaceutical agents capable of effectively treating HCV infection in patients afflicted with chronic hepatitis C. These studies have involved the use of interferon-alpha, alone and in combination with other antiviral agents. Such studies have shown that a substantial number of the participants do not respond to these therapies, and of those that do respond favorably, a large proportion were found to relapse after termination of treatment.

Until recently, interferon (IFN) was the only available therapy of proven benefit approved in the clinic for patients with chronic hepatitis C. However the sustained response rate is low, and interferon treatment also induces severe side-effects (i.e. retinopathy, thyroiditis, acute pancreatitis, depression) that diminish the quality of life of treated patients. Recently, interferon in combination with ribavirin has been approved for patients non-responsive to IFN alone. However, the side effects caused by IFN are not alleviated with this combination therapy. Pegylated forms of interferons such as PEG-Intron® and Pegasys® can apparently partially address these deleterious side-effects but antiviral drugs still remain the avenue of choice for oral treatment of HCV.

Therefore, a need exists for the development of effective antiviral agents for treatment of HCV infection that overcome the limitations of existing pharmaceutical therapies.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature nonstructural proteins (NS2, NS3, NS4A, NS4B, NS5A, and NS5B) is effected by two viral proteases. The first one, as yet poorly characterized, cleaves at the NS2-NS3 junction (henceforth referred to as NS2/3 protease); the second one is a serine protease contained within the N-terminal region of NS3 (NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protease with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

A general strategy for the development of antiviral agents is to inactivate virally encoded enzymes that are essential for the replication of the virus.

The following is a list of patent applications published in the last few years that disclose HCV NS3 protease inhibitor peptide analogs that are structurally different from the compounds of the present invention:
GB 2,337,262; JP10298151; JP 11126861; JP 11292840; JP 2001-103993; U.S. Pat Nos. 6,159,938; 6,187,905; WO 97/43310; WO 98/17679; WO 98/22496; WO 98/46597; WO 98/46630; WO 99/38888; WO 99/50230; WO 99/64442; WO 99/07733; WO 99/07734; WO 00/09543; WO 00/09558; WO 00/20400; WO 00/59929; WO 00/31129; WO 01/02424; WO 01/07407; WO 01/16357; WO 01/32691; WO 01/40262; WO 01/58929; WO 01/64678; WO 01/74768; WO 01/77113; WO 01/81325; WO 02/08187; WO 02/08198; WO 02/08244; WO 02/08251; WO 02/08256; WO 02/18369; WO 02/60926 and WO 02/79234.

One advantage of the present invention is that it provides tripeptide compounds that are inhibitory to the NS3 protease, an enzyme essential for the replication of the hepatitis C virus.

A further advantage of one aspect of the present invention resides in the fact that the compounds specifically inhibit the NS3 protease and do not show significant inhibitory activity against other serine proteases such as human leukocyte elastase (HLE), porcine pancreatic elastase (PPE), or bovine pancreatic chymotrypsin, or cysteine proteases such as human liver cathepsin B (Cat B). Furthermore, the compounds are active in cell culture and have good pharmacokinetic profile in vivo.

A further advantage of the present invention is that it provides compounds that are orally bioavailable in mammals.

SUMMARY OF THE INVENTION

Included in the scope of the invention is a compound of formula (I):

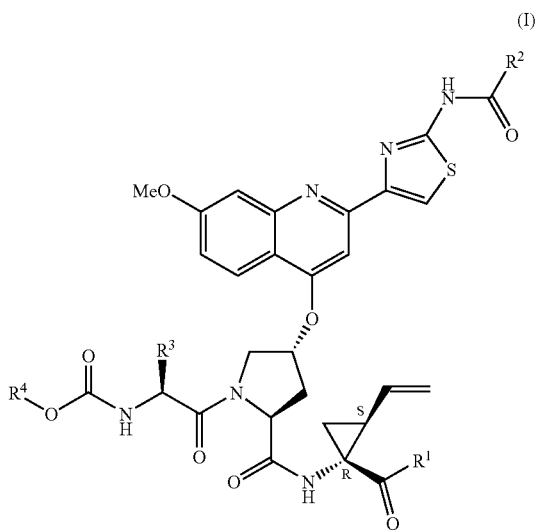

wherein $R^1$ is hydroxy or $NHSO_2R^{14}$ wherein $R^{14}$ is $(C_{1-8})$ alkyl, $(C_{3-7})$cycloalkyl or $\{(C_{1-6})alkyl\text{-}(C_{3-7})cycloalkyl\}$, which are all optionally substituted from 1 to 3 times with halo, cyano, nitro, $O\text{—}(C_{1-6})$alkyl, amido, amino or phenyl, or $R^{14}$ is $C_6$ or $C_{10}$ aryl which is optionally substituted from 1 to 3 times with halo, cyano, nitro, $(C_{1-6})$alkyl, $O\text{—}(C_{1-6})$alkyl, amido, amino or phenyl; $R^2$ is t-butyl, $-CH_2-C-(CH_3)_3$, or $-CH_2$-cyclopentyl; $R^3$ is t-butyl or cyclohexyl and $R^4$ is cyclobutyl, cyclopentyl, or cyclohexyl; or a pharmaceutically acceptable salt thereof.

Included within the scope of this invention is a pharmaceutical composition comprising an anti-hepatitis C virally effective amount of a compound of formula I, or a pharmaceutically acceptable salt thereof, in admixture with a pharmaceutically acceptable carrier medium or auxiliary agent.

According to one embodiment, the pharmaceutical composition of this invention further comprises interferon (pegylated or not), or ribavirin, or one or more other anti-HCV agent, or any combination of the above.

Another important aspect of the invention involves a method of treating a hepatitis C viral infection in a mammal by administering to the mammal an anti-hepatitis C virally effective amount of a compound of formula I, a pharmaceutically acceptable salt thereof, or a composition as described above, alone or in combination with one ore more of: interferon (pegylated or not), or ribavirin, or one or more other anti-HCV agents, all of which are administered together or separately, e.g., prior to, concurrently with or following the administration of the compound of formula I or pharmaceutically acceptable salt thereof.

Another important aspect of the invention involves a method of preventing a hepatitis C viral infection in a mammal by administering to the mammal an anti-hepatitis C virally effective amount of a compound of formula I, a pharmaceutically acceptable salt thereof, or a composition as described above, alone or in combination with one or more of: interferon (pegylated or not), or ribavirin, or one or more other anti-HCV agents, all of which administered together or separately, e.g., prior to, concurrently with or following the administration of the compound of formula I or pharmaceutically acceptable salt thereof.

Also within the scope of this invention is the use of a compound of formula I, as described herein, for the manufacture of a medicament for the treatment or prevention of hepatitis C viral infection.

DETAILED DESCRIPTION OF PREFERRED EMBODIMENTS

Definitions

As used herein, the following definitions apply unless otherwise noted:

With reference to the instances where (R) or (S) is used to designate the absolute configuration of a substituent or asymmetric centre of a compound of formula I, the designation is done in the context of the whole compound and not in the context of the substituent or asymmetric centre alone.

The designation "P1, P2, and P3" as used herein refer to the position of the amino acid residues starting from the C-terminus end of the peptide analogs and extending towards the N-terminus (i.e. P1 refers to position 1 from the C-terminus, P2: second position from the C-terminus, etc.) (see Berger A. & Schechter I., Transactions of the Royal Society London series B257, 249–264 (1970)).

As used herein the term "(1R, 2S)-vinyl-ACCA" refers to a compound of formula:

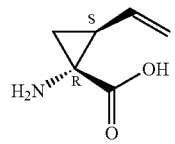

namely, (1R, 2S) 1-amino-2-ethenylcyclopropylcarboxylic acid.

The term "$(C_{1-6})$alkyl" as used herein, either alone or in combination with another substituent, means acyclic, straight or branched chain alkyl substituents containing from 1 to 6 carbon atoms and includes, for example, methyl, ethyl, propyl, butyl, 1-methylethyl, 1-methylpropyl, 2-methylpropyl, 1,1-dimethylethyl and hexyl. Similarly, the term "$(C_{1-8})$alkyl" means acyclic, straight of branched chain alkyl containing 1 to 8 carbon atoms, e.g. octyl.

The term "$(C_{3-7})$cycloalkyl" as used herein, either alone or in combination with another substituent, means a cycloalkyl substituent containing from 3 to 7 carbon atoms and includes cyclopropyl, cyclobutyl, cyclopentyl, cyclohexyl and cycloheptyl.

The term "$\{(C_{1-6})alkyl\text{-}(C_{3-7})cycloalkyl\}$" as used herein means a cycloalkyl radical containing from 3 to 7 carbon atoms directly linked to an alkylene radical containing 1 to 6 carbon atoms; for example, cyclopropylmethyl, cyclopentylethyl, cyclohexylmethyl, cyclohexylethyl and cycloheptylpropyl. In the instance where $R^{4A}$ is a $\{(C_{1-6})$alkyl-$(C_{3-6})cycloalkyl\}$, this group is attached to the $SO_2$ group via the $(C_{1-6})$alkyl (i.e. the alkylene portion).

The term "$C_6$ or $C_{10}$ aryl" as used herein, either alone or in combination with another radical, means either an aromatic monocyclic group containing 6 carbon atoms or an aromatic bicyclic group containing 10 carbon atoms. For example, aryl includes phenyl, 1-naphthyl or 2-naphthyl.

The term "$O\text{—}(C_{1-6})$alkyl" as used herein, either alone or in combination with another radical, means the radical —O—$(C_{1-6})$alkyl wherein alkyl is as defined above containing up to six carbon atoms, and includes methoxy, ethoxy, propoxy, 1-methylethoxy, butoxy and 1,1-dimethylethoxy. The latter radical is known commonly as tert-butoxy.

The term "halo" as used herein means a halogen substituent selected from bromo, chloro, fluoro or iodo.

The term "pharmaceutically acceptable salt" means a salt of a compound of formula (I) which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1–19, which is hereby incorporated by reference in its entirety.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, sulfuric acid, sulfamic acid, nitric acid, phosphoric acid, and the like, and organic acids such as acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "antiviral agent" as used herein means an agent (compound or biological) that is effective to inhibit the formation and/or replication of a virus in a mammal. This includes agents that interfere with either host or viral mechanisms necessary for the formation and/or replication of a virus in a mammal. Antiviral agents include, for example, ribavirin, amantadine, VX-497 (merimepodib, Vertex Pharmaceuticals), VX-498 (Vertex Pharmaceuticals), Levovirin, Viramidine, Ceplene (maxamine), XTL-001 and XTL-002 (XTL Biopharmaceuticals).

The term "other anti-HCV agent" as used herein means those agents that are effective for diminishing or preventing the progression of hepatitis C related symptoms of disease. Such agents can be selected from: antiviral agents, immunomodulatory agents, inhibitors of HCV NS3 protease, inhibitors of HCV polymerase or inhibitors of another target in the HCV life cycle.

The term "immunomodulatory agent" as used herein means those agents (compounds or biologicals) that are effective to enhance or potentiate the immune system response in a mammal. Immunomodulatory agents include, for example, class I interferons (such as α-, β-, δ- and omega interferons, tau-interferons, consensus interferons and asialo-interferons), class II interferons (such as γ-interferons) and pegylated interferons.

The term "inhibitor of HCV NS3 protease" as used herein means an agent (compound or biological) that is effective to inhibit the function of HCV NS3 protease in a mammal. Inhibitors of HCV NS3 protease include, for example, those compounds described in WO 99/07733, WO 99/07734, WO 00/09558, WO 00/09543, WO 00/59929 or WO 02/060926, and the Vertex/Eli Lilly pre-development candidate identified as VX-950 or LY-570310. Particularly, compounds #2, 3, 5, 6, 8, 10, 11, 18, 19, 29, 30, 31, 32, 33, 37, 38, 55, 59, 71, 91, 103, 104, 105, 112, 113, 114, 115, 116, 120, 122, 123, 124, 125, 126 and 127 disclosed in the table of pages 224–226 in WO 02/060926, can be used in combination with the compounds of the present invention.

The term "inhibitor of HCV polymerase" as used herein means an agent (compound or biological) that is effective to inhibit the function of an HCV polymerase in a mammal. This includes, for example, inhibitors of HCV NS5B polymerase. Inhibitors of HCV polymerase include non-nucleosides, for example, those compounds described in:

U.S. application Ser. No. 10/198,680, herein incorporated by reference in its entirety, which corresponds to PCT/CA02/01127, both filed 18 Jul. 2002 (Boehringer Ingelheim), U.S. application Ser. No. 10/198,384, herein incorporated by reference in its entirety, which corresponds to PCT/CA02/01128, both filed 18 Jul. 2002 (Boehringer Ingelheim), U.S. application Ser. No. 10/198,259, herein incorporated by reference in its entirety, which corresponds to PCT/CA02/01129, both filed 18 Jul. 2002 (Boehringer Ingelheim), WO 02/100846 A1 and WO 02/100851 A2 (both Shire), WO 01/85172 A1 and WO 02/098424 A1 (both GSK), WO 00/06529 and WO 02/06246 A1 (both Merck), WO 01/47883 and WO 03/000254 (both Japan Tobacco) and EP 1 256 628 A2 (Agouron).

Furthermore other inhibitors of HCV polymerase also include nucleoside analogs, for example, those compounds described in:

WO 01/90121 A2 (Idenix),
WO 02/069903 A2 (Biocryst Pharmaceuticals Inc.), and
WO 02/057287 A2 and WO 02/057425 A2 (both Merck/Isis).

Specific examples of inhibitors of an HCV polymerase, include JTK-002, JTK-003 and JTK-109 (Japan Tobacco).

The term "inhibitor of another target in the HCV life cycle" as used herein means an agent (compound or biological) that is effective to inhibit the formation and/or replication of HCV in a mammal other than by inhibiting the function of the HCV NS3 protease. This includes agents that interfere with either host or HCV viral mechanisms necessary for the formation and/or replication of HCV in a mammal. Inhibitors of another target in the HCV life cycle include, for example, agents that inhibit a target selected from a helicase and an HCV NS2/3 protease. Specific examples of inhibitors of another target in the HCV life cycle include JTK-003/002 (Japan Tobacco) and ISIS-14803 (ISIS Pharmaceuticals).

The term "HIV inhibitor" as used herein means an agents (compound or biological) that is effective to inhibit the formation and/or replication of HIV in a mammal. This includes agents that interfere with either host or viral mechanisms necessary for the formation and/or replication of HIV in a mammal. HIV inhibitors include, for example, nucleosidic inhibitors, non-nucleosidic inhibitors, protease inhibitors, fusion inhibitors and integrase inhibitors.

The term "HAV inhibitor" as used herein means an agent (compound or biological) that is effective to inhibit the formation and/or replication of HAV in a mammal. This includes agents that interfere with either host or viral mechanisms necessary for the formation and/or replication of HAV in a mammal. HAV inhibitors include Hepatitis A vaccines, for example, Havrix® (GlaxoSmithKline), VAQTA® (Merck) and Avaxim® (Aventis Pasteur).

The term "HBV inhibitor" as used herein means an agent (compound or biological) that is effective to inhibit the formation and/or replication of HBV in a mammal. This includes agents that interfere with either host or viral mechanisms necessary for the formation and/or replication of HBV in a mammal. HBV inhibitors include, for example, agents that inhibit HBV viral DNA polymerase or HBV vaccines. Specific examples of HBV inhibitors include Lamivudine (Epivir-HBV®), Adefovir Dipivoxil, Entecavir, FTC (Coviracil®), DAPD (DXG), L-FMAU (Clevudine®), AM365 (Amrad), Ldt (Telbivudine), monoval-LdC (Valtorcitabine), ACH-126,443 (L-Fd4C) (Achillion), MCC478 (Eli Lilly), Racivir (RCV), Fluoro-L and D nucleosides, Robustaflavone, ICN 2001-3 (ICN), Bam 205 (Novelos), XTL-001 (XTL), Imino-Sugars (Nonyl-DNJ) (Synergy), HepBzyme; and immunomodulator products such as: interferon alpha 2b, HE2000 (Hollis-Eden), Theradigm (Epimmune), EHT899 (Enzo Biochem), Thymosin alpha-1 (Zadaxin®), HBV DNA vaccine (PowderJect), HBV DNA vaccine (Jefferon Center), HBV antigen (OraGen), BayHep B® (Bayer), Nabi-HB® (Nabi) and Anti-hepatitis B (Cangene); and HBV vaccine products such as the following: Engerix B, Recombivax HB, GenHevac B, Hepacare, Bio-Hep B, TwinRix, Comvax, Hexavac.

The term "class I interferon" as used herein means an interferon selected from a group of interferons that all bind to receptor type I. This includes both naturally and synthetically produced class I interferons. Examples of class I interferons include α-, β-, omega interferons, tau-interferons, consensus interferons, asialo-interferons.

The term "class II interferon" as used herein means an interferon selected from a group of interferons that all bind to receptor type II. Examples of class II interferons include γ-interferons.

Specific preferred examples of some of these agents are listed below:

antiviral agents: ribavirin and amantadine;
immunomodulatory agents: class I interferons, class II interferons and pegylated interferons;
inhibitor of another target in the HCV life cycle that inhibits a target selected from NS3 helicase, HCV NS2/3 protease or internal ribosome entry site (IRES);
HIV inhibitors: nucleosidic inhibitors, non-nucleosidic inhibitors, protease inhibitors, fusion inhibitors and integrase inhibitors; or
HBV inhibitors: agents that inhibit HBV viral DNA polymerase or is an HBV vaccine.

As discussed above, combination therapy is contemplated wherein a compound of formula (1), or a pharmaceutically acceptable salt thereof, is co-administered with at least one additional agent selected from: an antiviral agent, an immunomodulatory agent, another inhibitor of HCV NS3 protease, an inhibitor of HCV polymerase, an inhibitor of another target in the HCV life cycle, an HIV inhibitor, an HAV inhibitor and an HBV inhibitor. Examples of such agents are provided in the Definitions section above. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of wherein a compound of formula (1), or a pharmaceutically acceptable salt thereof.

As used herein, the term "treatment" means the administration of a compound or composition according to the present invention to alleviate or eliminate symptoms of the hepatitis C disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood.

Preferred Embodiments

Preferred are compounds of formula 1 as defined above wherein $R^1$ is hydroxy, $NHSO_2Me$, $NHSO_2$-cyclopropyl, or $NHSO_2Ph$. More preferably, $R^1$ is $NHSO_2Me$ or hydroxy. Most preferably, $R^1$ is hydroxy.

Preferred are compounds of formula 1 as defined above wherein $R^2$ is t-butyl or $CH_2-C(CH_3)_3$. More preferably, $R_2$ is $CH_2-C(CH_3)_3$. Preferably $R^3$ is t-butyl.

Preferably, compounds of formula 1 as defined above wherein $R^4$ is cyclopentyl or cyclohexyl. More preferably $R^4$ is cyclopentyl.

More preferably, a compound of formula 1 as defined above wherein $R^1$ is hydroxy, $R^2$ is $CH_2-C(CH_3)_3$, $R^3$ is t-butyl and $R^4$ is cyclopentyl.

More preferably, a compound of formula I wherein $R^1$ is hydroxy, $R^2$ and $R^3$ each is t-butyl and $R^4$ is cyclopentyl.

More preferably, a compound of formula 1 wherein $R^1$ is hydroxy, $R^2$ is $CH_2-C(CH_3)_3$, $R^3$ is cyclohexyl and $R^4$ is cyclopentyl.

More preferably, a compound of formula 1 wherein $R^1$ is hydroxy, $R^2$ is $CH_2$—$C(CH_3)_3$, and $R^3$ and $R^4$ each is cyclohexyl.

More preferably, a compound of formula 1 wherein $R^1$ is hydroxy, $R^2$ is cyclopentylmethyl, $R^3$ is t-butyl, and $R^4$ is cyclobutyl.

More preferably, a compound of formula 1 wherein $R^1$ is hydroxy, $R^2$ is $CH_2$—$C(CH_3)_3$, $R^3$ is t-butyl and $R^4$ is cyclobutyl.

More preferably, a compound of formula 1 wherein $R^1$ is $NHSO_2Me$, $R^2$ is $CH_2$—$C(CH_3)_3$ $R^3$ is t-butyl and $R^4$ is cyclopentyl.

More preferably, a compound of formula 1 wherein $R^1$ is $NHSO_2Ph$, $R^2$ is $CH_2$—$C(CH_3)_3$, $R^3$ is t-butyl and $R^4$ is cyclopentyl.

According to an alternate embodiment, the pharmaceutical composition of this invention may additionally comprise another anti-HCV agent. Examples of anti-HCV agents include, α- (alpha), β- (beta), δ- (delta), γ- (gamma) or ω- (omega) interferon, ribavirin and amantadine.

According to another alternate embodiment, the pharmaceutical composition of this invention may additionally comprise another inhibitor of HCV NS3 protease.

According to another alternate embodiment, the pharmaceutical composition of this invention may additionally comprise an inhibitor of HCV polymerase.

According to yet another alternate embodiment, the pharmaceutical composition of this invention may additionally comprise an inhibitor of other targets in the HCV life cycle, including but not limited to, helicase, NS2/3 protease or internal ribosome entry site (IRES).

The pharmaceutical composition of this invention may be administered orally, parenterally or via an implanted reservoir. Oral administration or administration by injection is preferred. The pharmaceutical composition of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

The pharmaceutical composition may be in the form of a sterile injectable preparation, for example, as a sterile injectable aqueous or oleaginous suspension. This suspension may be formulated according to techniques known in the art using suitable dispersing or wetting agents (such as, for example Tween 80) and suspending agents.

The pharmaceutical composition of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Other suitable vehicles or carriers for the above noted formulations and compositions can be found in standard pharmaceutical texts, e.g. in "Remington's Pharmaceutical Sciences", The Science and Practice of Pharmacy, 19$^{th}$ Ed. Mack Publishing Company, Easton, Pa., (1995).

Dosage levels of between about 0.01 and about 100 mg/kg body weight per day, preferably between about 0.1 and about 50 mg/kg body weight per day of the protease inhibitor compound described herein are useful in a monotherapy for the prevention and treatment of HCV mediated disease. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the composition of this invention comprise a combination of a compound of formula I and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds or their pharmaceutically acceptable salts are formulated together with a pharmaceutically acceptable carrier, the resulting composition may be administered in vivo to mammals, such as man, to inhibit HCV NS3 protease or to treat or prevent HCV virus infection. Such treatment may also be achieved using a compound of this invention in combination with agents which include, but are not limited to: α-, β-, δ-, ω-, or γ-interferon, ribavirin, amantadine; other inhibitors of HCV NS3 protease; inhibitors of HCV polymerase; inhibitors of other targets in the HCV life cycle, which include but not limited to, helicase, NS2/3 protease, or internal ribosome entry site (IRES); or combinations thereof. The additional agents may be combined with compounds of this invention to create a single dosage form. Alternatively these additional agents may be separately administered to a mammal as part of a multiple dosage form.

Accordingly, another embodiment of this invention provides a method of inhibiting HCV NS3 protease activity in a mammal by administering a compound of the formula I.

In a preferred embodiment, this method is useful in decreasing the NS3 protease activity of the hepatitis C virus infecting a mammal.

If the pharmaceutical composition comprises only a compound of this invention as the active component, such method may additionally comprise the step of administering to said mammal an agent selected from an immunomodulatory agent, an antiviral agent, a HCV NS3 protease inhibitor, an inhibitor of HCV polymerase or an inhibitor of other targets in the HCV life cycle such as helicase, NS2/3 protease or IRES. Such additional agent may be administered to the mammal prior to, concurrently with, or following the administration of the composition of this invention.

A compound of formula 1 set forth herein may also be used as a laboratory reagent. A compound of this invention may also be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

A compound of formula 1 set forth herein may also be used as a research reagent. A compound of formula 1 may also be used as positive control to validate surrogate cell-based assays or in vitro or in vivo viral replication assays.

Further details of the invention are illustrated in the following examples which are understood to be non-limiting with respect to the appended claims.

EXAMPLES

Temperatures are given in degrees Celsius. Solution percentages express a weight to volume relationship, and solution ratios express a volume to volume relationship, unless stated otherwise. Nuclear magnetic resonance (NMR) spectra were recorded on a Bruker 400 MHz spectrometer; the chemical shifts (δ) are reported in parts per million. Flash chromatography was carried out on silica gel ($SiO_2$) according to Still's flash chromatography technique (W. C. Still et al., J. Org. Chem., (1978), 43, 2923).

Abbreviations used in the examples include: DBU: 1,8-diazabicyclo[5.4.0]undec-7-ene; DCM: dichloromethane; DIEA: diisopropylethylamine; DIPEA: diisopropylethylamine; DMF: N,N-dimethylformamide; DMAP: 4-(dimethylamino)pyridine; EtOAc: ethyl acetate; HATU: [O-7-azabenzotriazol-1-yl)-1,1,3,3-tetramethyluronium hexafluorophosphate]; HPLC: high performance liquid chromatography; MS: mass spectrometry (MALDI-TOF: Matrix Assisted Laser Disorption Ionization-Time of Flight, FAB: Fast Atom Bombardment); Me: methyl; MeOH: methanol; Ph: phenyl; R.T.: room temperature (18 to 220); tert-butyl or t-butyl: 1,1-dimethylethyl; Tbg: tert-butyl glycine: tert-leucine; TFA: trifluoroacetic acid; and THF: tetrahydrofuran.

Synthesis of Compounds of Formula (I):

In general, the compounds of formula 1, and intermediates therefore, are prepared by known methods using reaction conditions which are known to be suitable for the reactants. Several such methods are disclosed in WO 00/09543, WO 00/09558 and U.S. Pat. No. 6,323,180, incorporated herein by reference.

Preparation of Thioureas

Preparation of Thiourea 2a

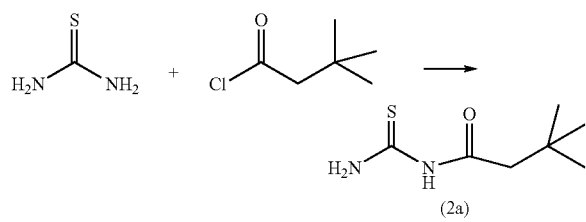

Thiourea (5.0 gm, 66 mmol) was dissolved in toluene (50 mL) and tert-butylacetyl chloride (8.88 gm, 66 mmol) was added. The mixture was heated at reflux for 14 h to give a yellow solution. The mixture was concentrated to dryness, and the residue partitioned between EtOAc and sat. $NaHCO_3$. The yellow organic phase was dried over $MgSO_4$, filtered and concentrated to give a yellow solid. The solid was dissolved into a minimum amount of EtOAc and triturated with hexane to give 2a as a white solid (8.52 g; 75%). M.S. (electrospray): 173 (M−H)−175 (M+H)+. Reverse Phase HPLC Homogeneity (0.06% TFA; $CH_3CN:H_2O$): 99%.

Preparation of Thiourea 2b

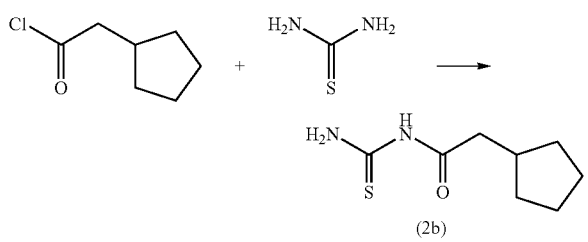

Using the procedure described above and using commercially available cyclopentyl acetyl chloride instead of tert-butylacetyl chloride yielded thiourea 2b.

Synthesis of Intermediates 3

Preparation of Carbamate 3a

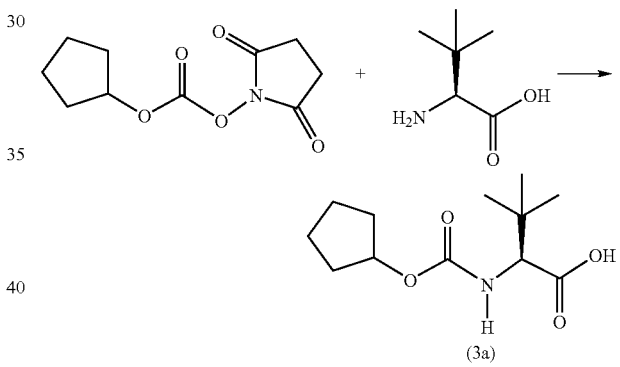

Tetrahydrofuran (350 mL) was added to a flask containing carbonic acid cyclopentyl ester 2,5-dioxo-pyrrolidin-1-yl ester (9.00 g; 39.6 mmol) and tert-leucine (6.24 g; 47.5 mmol) resulting in a suspension. Distilled water(100 mL) was added with vigorous stirring. A small amount of solid remained undissolved. Triethylamine (16.6 mL; 119 mmol) was then added resulting in a homogenous solution which was stirred at R.T. After 2.5 h, the THF was evaporated and the aqueous residue diluted with water (100 mL) and the reaction rendered basic by the addition of 1 N NaOH (25 mL—final pH>10). The solution was washed with EtOAc (2×200 mL) and the aqueous phase then acidified with 1 N HCl (ca. 70 mL—final pH<2). The turbid solution was extracted with EtOAc (200+150 mL). The extract was dried ($MgSO_4$) and evaporated to give compound 3a as a white solid (8.68 g).

Preparation of Carbamates 3b, 3c, and 3d

Using the procedure described above and using appropriate combinations of tert-butyl glycine, or cyclohexyl glycine and carbonic acid cyclobutyl, cyclopentyl, or cyclohexyl ester 2,5-dioxo-pyrrolidin-1-yl ester, the following carbamates were prepared:

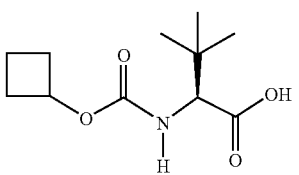

3b

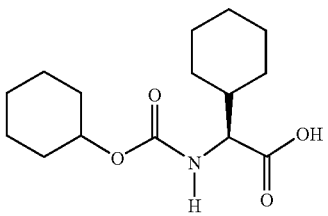

3c

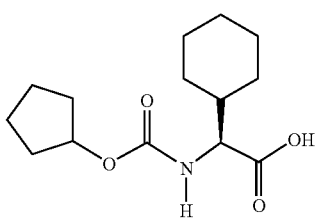

3d

Preparation of Intermediate 5

Preparation of Intermediate 5a:

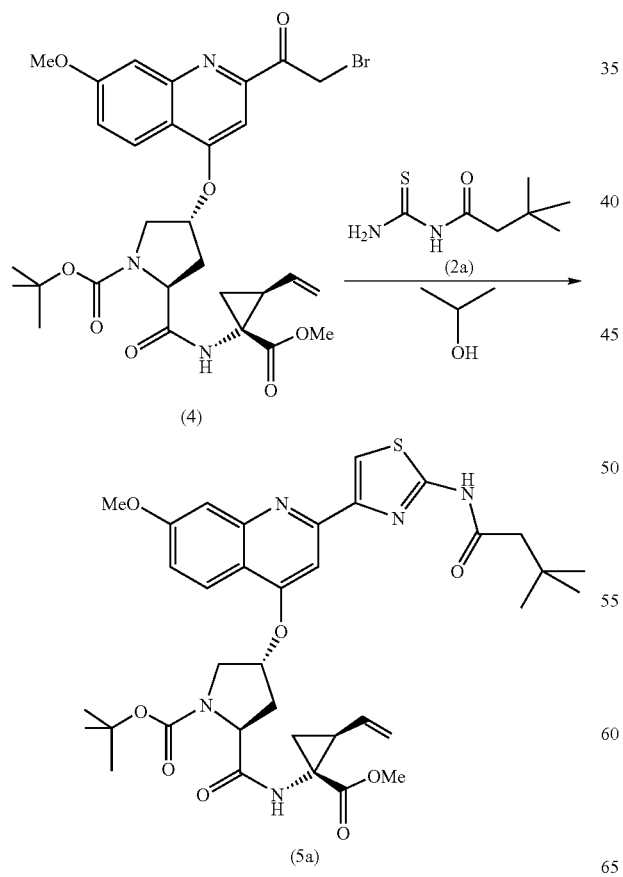

α-Bromoketone 4 (3.61 g; 5.71 mmol) was combined with thiourea 2a (1.09 g; 6.28 mmol) in isopropanol (140 mL) and the yellow solution was placed into a pre-heated oil bath of 70° C. for 1.5 h. The solution was cooled to R.T. and evaporated to dryness. The residue was dissolved in EtOAc. The EtOAc solution was washed with saturated $NaHCO_3$ (2×), water (2×) and brine (1×), dried ($MgSO_4$), and evaporated to give the product as an orange-brown foam. Flash column chromatography in 7:3 hexane:EtOAc removed the less polar impurities and 6:4 hexane:EtOAc provided pure product as a light yellow solid (3.05 g; 76%). M.S.(electrospray): 706.3 (M–H)– 708.4 (M+H)+. Reverse Phase HPLC Homogeneity (0.06% TFA; $CH_3CN:H_2O$): 99%.

Preparation of Intermediate 5b:

Using the procedure described above and using thiourea 2b instead of thiourea 2a, the corresponding intermediate 5b is obtained:

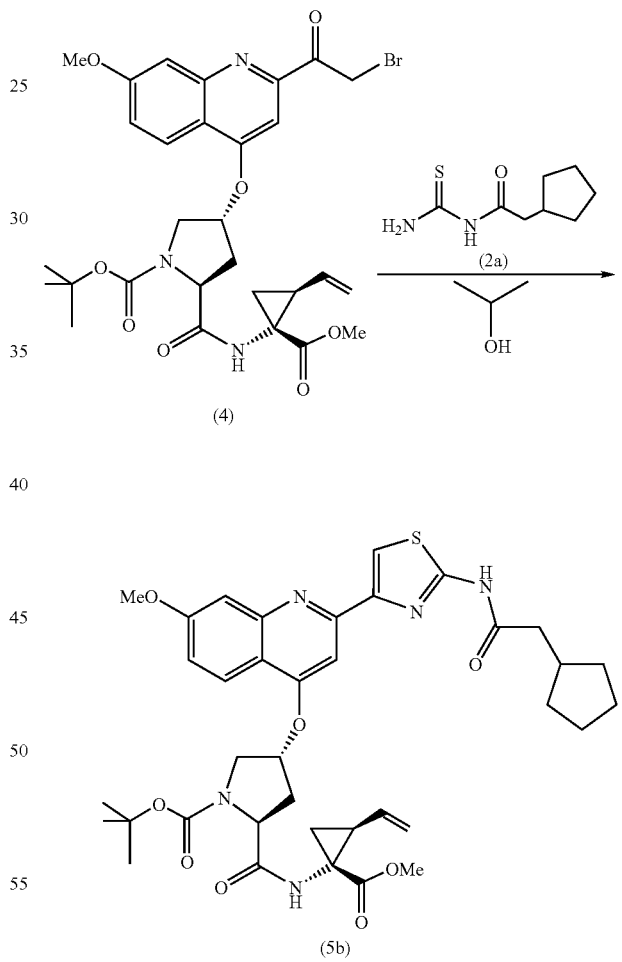

Preparation of Intermediate 5c:

Using the procedure described above and using commercially available thiourea instead of thiourea 2a, the corresponding intermediate 5c is obtained:

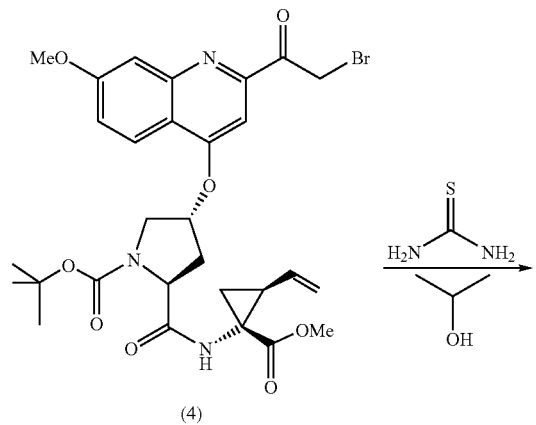
(4)
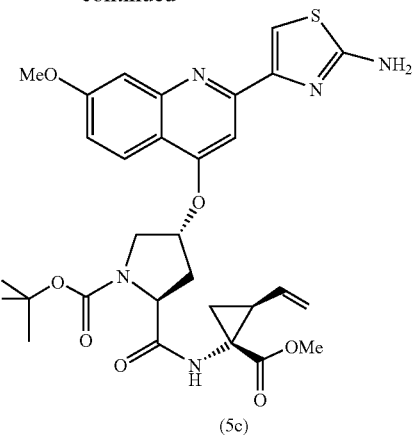
(5c)
Example 1
Synthesis of Compound 100
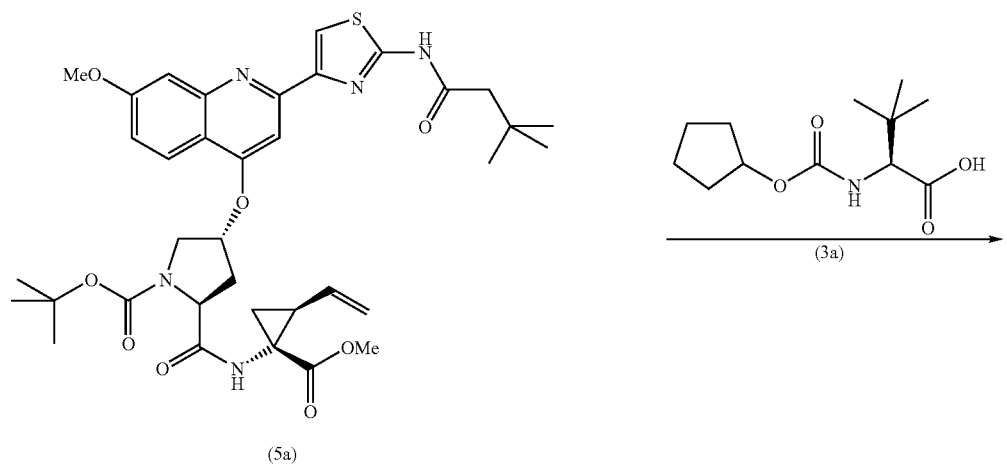
(5a)
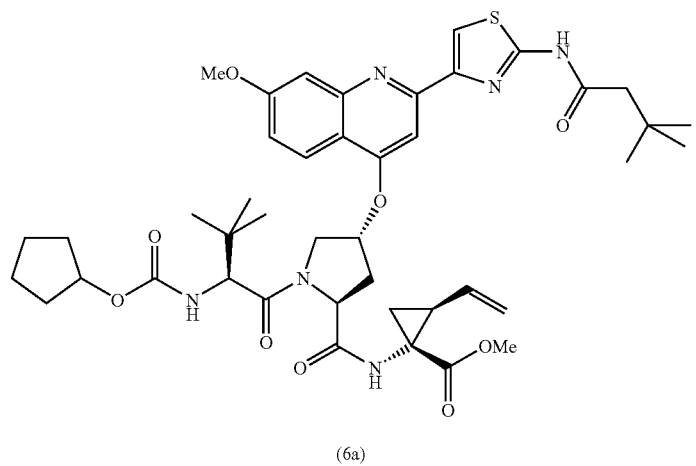
(6a)

Step 1: Preparation of Intermediate 6a

Boc-Dipeptide 5a (3.05 g; 4.31 mmol) was dissolved in 4 N HCl/dioxane (22 mL). After stirring at R.T. for 30 min., the HCl salt precipitated. MeOH (2 mL) was added to dissolve the precipitate. After 2 h, the reaction mixture was evaporated to dryness. The resulting HCl salt was dissolved in DCM (22 mL) and DIEA (3.0 mL; 17.24 mmol); carbamate 3a (1.15 g ; 4.47 mmol) and HATU (1.72 g ; 4.516 mmol) were added. The solution was stirred at R.T. for 6 h. The mixture was then diluted with EtOAc and the solution washed with saturated $NaHCO_3$ (2×), water (2×) and brine (1×), dried (MgSO4), filtered and evaporated to obtain compound 6a as a yellow solid. Flash column chromatography eluting first with hexane:EtOAc 7:3 and then 6:4 afforded pure Me-ester 6a as a white foam (3.25 g; 90%). M.S. (electrospray): 831.4 (M−H)− 833.4 (M+H)+ 855.4 (M+Na)+. Reverse Phase HPLC Homogeneity (0.06% TFA; $CH_3CN:H_2O$): 98%.

Step 2: Hydrolysis of Ester separated and the aqueous layer further extracted with EtOAc (2×). The combined EtOAc extracts were washed with deionized water (2×), deionized water prepared brine (1×), dried ($MgSO_4$), filtered and evaporated to obtain compound 100 as a pale yellow-white solid (3.02 g; 95% yield).

Conversion to Na Salt:

The neutral compound 100 (1.22 g; 1.49 mmol) was dissolved in MeOH (30 mL) and 1 equivalent 0.01N NaOH (14.85 mL) was added—no product precipitation. The clear yellow solution was concentrated, diluted with deionized water, frozen and lyophilized to obtain the product (Na salt) as a yellow-white amorphous solid (1.24 g; 99% yield)

Na Salt: MW: 840.98 $C_{42}H_{53}N_6O_9SNa$

M.S.(electrospray): 817.3 (M−H)− 819.4 (M+H)+ 841.4 (M+Na)+. Reverse Phase HPLC Homogeneity (0.06% TFA; $CH_3CN:H_2O$): 98%.

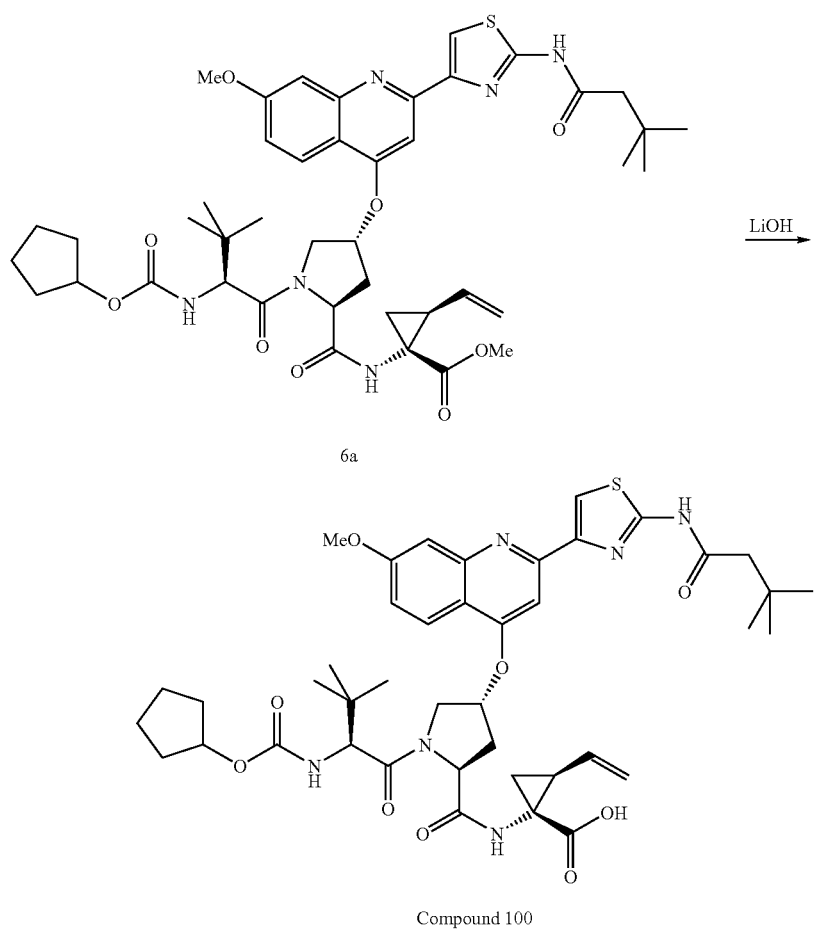

Compound 100

Methyl ester 6a (3.24 mg; 3.89 mmol) was dissolved in THF (40 mL) and MeOH (20 mL), and an aqueous solution of LiOH (1.63 mg; 38.9 mmol in 25 mL) was added. The yellow reaction mixture was stirred for 5.5 h and then concentrated to provide an off-white suspension. The suspension was dissolved in EtOAc and brine, prepared with deionized water. The pH of the resulting solution was adjusted to 6 by the addition of 1N HCl. The layers were $^1$H NMR (400 MHz,DMSO-$d_6$): ca, 6:1 mixture of rotamers; δ 8.11–7.65 (m, 4H), 7.33 (bs, 1H), 7.18–6.97 (m, 2H), 6.36–6.08 (m, 1H), 5.55–5.33 (m, 1H), 4.98 (d, J=18.0 Hz, 1H), 4.85 (bs, 1H), 4.80 (d, J=10.4 Hz, 1H), 4.50–4.41 (m, 1H), 4.22–4.02 (m, 2H), 3.92 (s, 3H), 2.72–2.45 (m, 1H), 2.50 (under DMSO, s, 2H), 2.40–2.26 (m, 1H), 1.89–1.43 (m, 9H), 1.37–1.30 (m, 1H), 1.30–1.12 (m, 1H), 1.03 & 0.90 (2×s, 9H), 0.98 & 0.94 (2×s, 9H).

Example 2

Synthesis of Compound 101

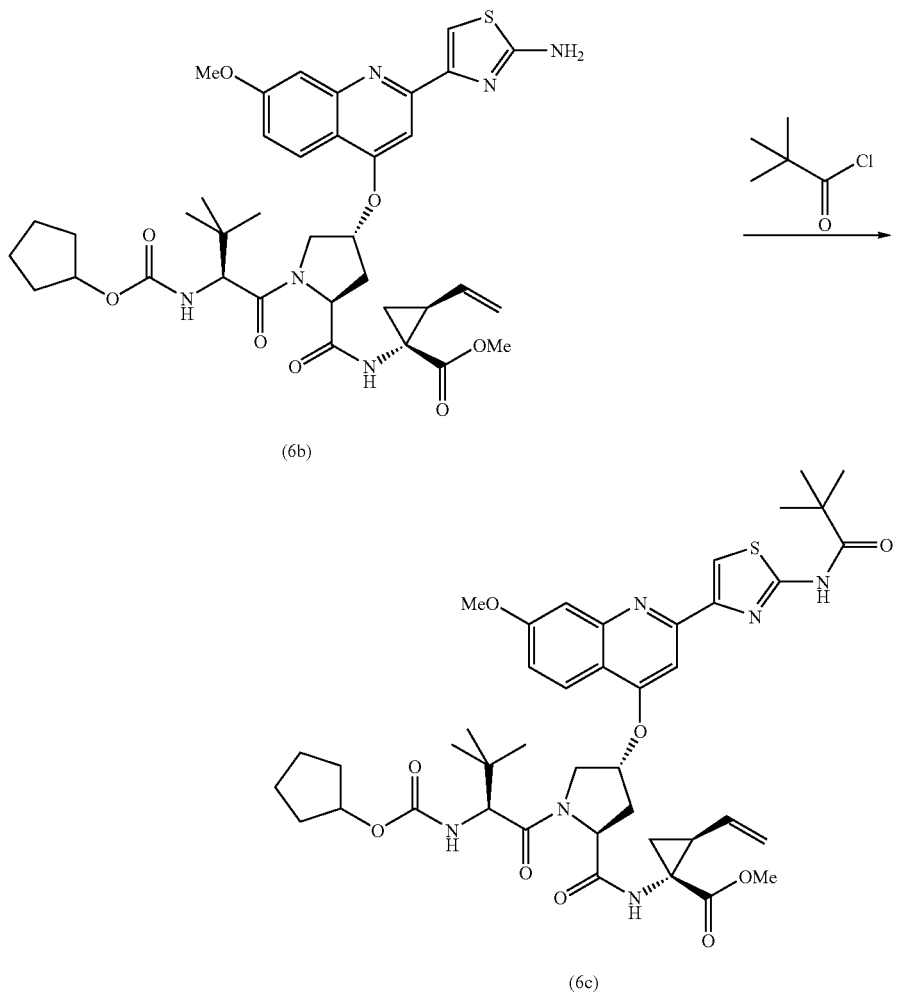

By following the same procedure as described in the first step of example 1, and using Boc-dipeptide 5c instead of 5a, compound 6b was obtained.

Compound 6b (70 mg, 0.095 mmol) was dissolved in 2 mL of DCM and successively treated with DIEA (0.045 mL, 0.26 mmol) and pivaloyl chloride (0.015 mL, 0.12 mmol). After stirring for 1 h at 40° an additional pivaloyl chloride (0.015 mL, 0.12 mmol) was added and stirring was continued for an additional 2 h. After the solution was concentrated, the residue was dissolved in EtOAc. The solution was washed with a saturated solution of NaHCO$_3$ and brine, dried (MgSO$_4$) and concentrated to afford 82 mg of crude compound 6c which was used without purification.

Methyl ester derivative 6c was hydrolyzed as in step 2 of example 1 and purified by preparative HPLC using a YMC Combi-Prep. ODS-AQ column, 50×20 mm. ID, S-5micron, 120 A, and a linear gradient program from 2 to 100% AcCN/water (0.06% TFA).

Fractions were analyzed by analytical HPLC, and the pure fractions were combined, concentrated, frozen and lyophilized to yield compound 101 as the trifluoroacetate salt:

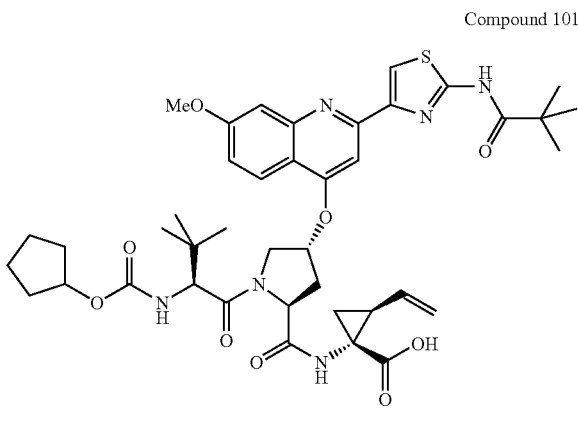

Compound 101

$^1$H NMR (400 MHz, DMSO-d$_6$): ca, 85:15 mixture of rotamers, major isomer description; δ 8.56 (s, 1H), 8.40–8.22 (m, 1H), 8.17 (d, J=8.9 Hz, 1H), 7.67 (bs, 1H), 7.52 (bs, 1H), 7.24–7.15 (m, 1H), 7.03 (d, J=8.3 Hz, 1H), 5.78–5.67 (m, 1H), 5.61–5.53 (m, 1H), 5.19 (dd, J=17.2, 1.6 Hz, 1H), 5.09–5.03 (m, 1H), 4.63–4.55 (m, 1H), 4.49–4.39 (m, 2H), 4.11–3.92 (m, 2H), 3.95 (s, 3H), 2.62–2.53 (m, 1H), 2.33–2.25 (m, 1H), 2.06–1.98 (m, 1H), 1.72–1.25 (m, 10H), 1.30 (s, 9H), 0.97 (s, 9H).

M.S.(electrospray): 803.3 (M–H)– 805.3 (M+H)+. Reverse Phase HPLC Homogeneity (0.06% TFA; CH₃CN:H₂O): 97%

Example 3

Preparation of Compound 102

By following the procedure described in example 1 and using carbamate 3d instead of 3a and using preparative HPLC to purify the final compound as described in example 2, compound 102 was obtained as the trifluoroacetate salt:

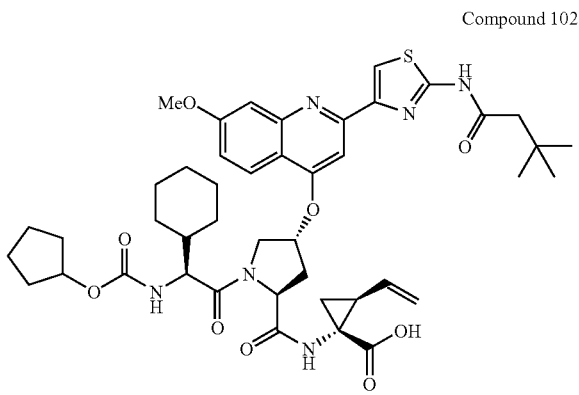

Compound 102

¹H NMR (400 MHz,DMSO-d₆): ca, 90:10 mixture of rotamers, major isomer description; δ12.37 (s, 1H), 8.54 (s, 1H), 8.40–8.06 (m, 2H), 7.67–7.40 (m, 2H), 7.26 (d, J=8.0 Hz, 1H), 7.26–7.13 (m, 1H), 5.77–5.65 (m, 1H), 5.62–5.49 (m, 1H), 5.23–5.16 (m, 1H), 5.10–5.03 (m, 1H), 4.57–4.37 (m, 3H), 4.03–3.88 (m, 2H), 3.94 (s, 3H), 2.64–2.54 (m, 1H), 2.41 (s, 2H), 2.37–2.22 (m, 1H), 2.04–1.95 (m, 1H), 1.79–1.21 (m, 16H), 1.17–0.85 (m, 5H), 1.04 (s, 9H). M.S.(electrospray): 843.5 (M–H)– 845.4 (M+H)+. Reverse Phase HPLC Homogeneity (0.06% TFA; CH₃CN:H₂O): 99%

Example 4

Preparation of Compound 103

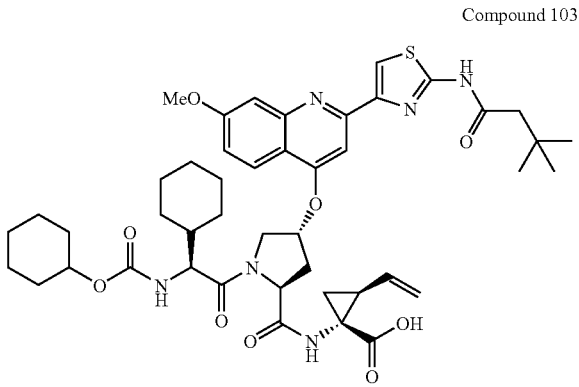

Compound 103

By following the procedure described in example 1 but using carbamate 3c instead of 3a and using preparative HPLC to purify the final compound as described in example 2, compound 103 was obtained as the trifluoroacetate salt:

¹H NMR (400 MHz,DMSO-d₆): ca, 85:15 mixture of rotamers, major isomer description; δ12.35 (s, 1H), 8.52 (m, 1H), 8.43–8.06 (m, 2H), 7.67–7.41 (m, 2H), 7.26 (d, J=7.8 Hz, 1H), 7.24–7.11 (m, 1H), 5.77–5.65 (m, 1H), 5.62–5.48 (m, 1H), 5.23–5.15 (m, 1H), 5.10–5.03 (m, 1H), 4.52–4.38 (m, 2H), 4.15–4.05 (m, 1H), 4.03–3.89 (m, 2H), 3.94 (s, 3H), 2.63–2.52 (m, 1H), 2.41 (s, 2H), 2.35–2.23 (m, 1H), 2.05–1.96 (m, 1H), 1.81–1.41 (m, 11H), 1.38–0.86 (m, 12H), 1.04 (s, 9H). M.S.(electrospray): 857.5 (M–H)– 859.4 (M+H)+. Reverse Phase HPLC Homogeneity (0.06% TFA; CH₃CN:H₂O): 99%

Example 5

Preparation of Compound 104

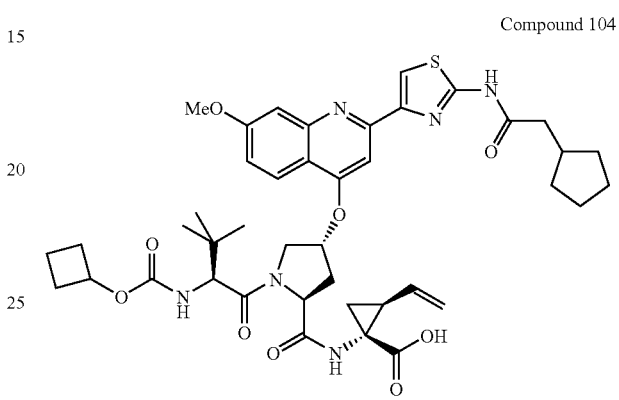

Compound 104

By following the procedure described in example 1 but using carbamate 3b instead of 3a and Boc-dipeptide 5b instead of 5a and using preparative HPLC to purify the final compound as described in example 2, compound 104 was obtained as the trifluoroacetate salt:

¹H NMR (400 MHz,DMSO-d₆): ca, 3:1 mixture of rotamers; δ8.02 (s, 1H), 7.90 (s, 1H), 7.84 (d, J=7.0 Hz, 1H),7.70 (s, 1H) 7.33 (d, J=2.2 Hz, 1H), 7.14 (dd, J=2.5, 8.2 Hz, 1H), 7.09 (dd, J=2.2, 9.2 Hz, 1H), 6.29–6.08 (m, 1H), 5.54–5.32 (m, 1H), 4.99 (d, J=15.9 Hz, 1H), 4.80 (d, J=10.0 Hz, 1H), 4.76–4.64 (m, 1H), 4.46 (dd, J=6.7, 13.9 Hz, 1H), 4.19–4.08 (m, 3H), 3.92 (s, 3H), 2.70–2.61 (m, 2H), 2.37–2.09 (m, 4H), 2.03–1.82 (m, 1H), 1.85 (bs, 2H), 1.77–1.44 (m, 8H), 1.35–1.29 (m, 1H), 1.29–1.15 (m, 4H), 0.98 & 0.90 (2×s, 9H). M.S.(electrospray): 815.3 (M–H)– 817.3 (M+H)+. Reverse Phase HPLC Homogeneity (0.06% TFA; CH₃CN:H₂O): 98%.

Example 6

Preparation of Compound 105

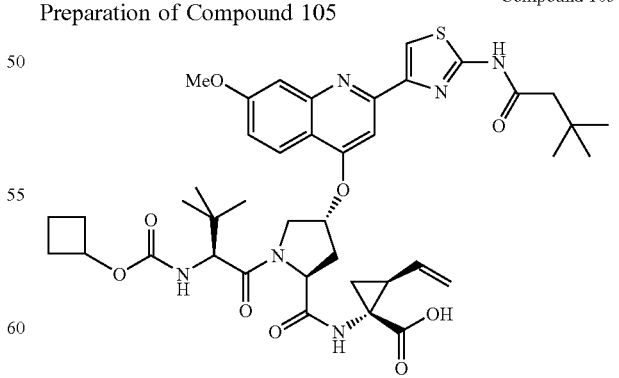

Compound 105

By following the procedure described in example 1 but using carbamate 3b instead of 3a and using preparative HPLC to purify the final compound as described in example 2, compound 105 was obtained as the trifluoroacetate salt:

$^1$H NMR (400 MHz, DMSO-d$_6$): ca, 7:1 mixture of rotamers; δ8.58 (s, 1H), 8.19 (d, J=8.0 Hz, 1H), 7.76–7.50 (m, 2H), 7.35–7.20 (m, 1H), 7.19 (d, J=8.0 Hz, 1H), 5.78–5.67 (m, 1H), 5.65–5.50 (m, 1H), 5.19 (d, J=17.0 Hz, 1H), 5.07 (d, J=10.2 Hz, 1H), 4.51–4.42 (m, 2H), 4.42–4.31 (m, 1H), 4.02 (d, J=7.4 Hz, 1H), 4.02–3.93 (m, 1H), 3.97 (s, 3H), 2.63–2.52 (m, 1H), 2.42 (s, 2H), 2.35–2.25 (m, 1H), 2.07–1.95 (m, 3H), 1.90–1.76 (m, 1H), 1.70–1.41 (m, 3H), 1.30–1.23 (m, 1H), 1.04 (s, 9H), 0.96 & 0.87 (2×s, 9H), M.S.(electrospray): 803.4 (M−H)− 805.4 (M+H)+. Reverse Phase HPLC Homogeneity (0.06% TFA; CH$_3$CN:H$_2$0): 98%.

Example 7

Preparation of Compound 106

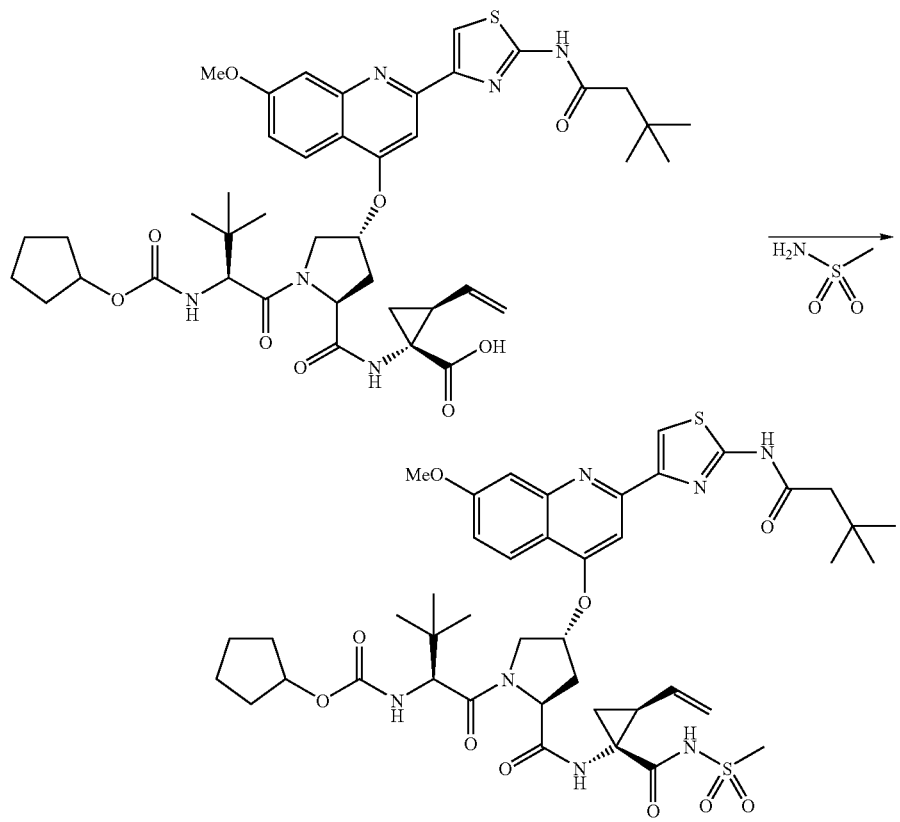

Compound 106

Compound 100 of example 1 (29.8 mg, 0.036 mmol) was combined with HATU (1.2 equiv., 19.7 mg, 0.052 mmol) and dissolved in anhydrous DMF (4 mL). The solution was stirred at R.T. and DIPEA (5 equiv., 31.4 μL, 0.18 mmol) was added dropwise over ca. 1 min. The mixture was stirred for 20 min. at R.T. and analyzed by analytical HPLC for the formation of the activated ester. A solution of methanesulfonamide (5.8 equiv., 19.7 mg, 0.207 mmol), DMAP (5.4 equiv., 23.5 mg, 0.193 mmol) and DBU (4.8 equiv., 25.8 μL, 0.172 mmol) was added in DMF (1 mL). The reaction mixture was stirred 16 h at R.T. before being concentrated in vacuo. The residue was reconstituted in DMSO and purified by preparative HPLC. Lyophilization gave the final product (23 mg, 71.3%) as an off-white amorphous solid.

$^1$H-NMR (400 MHz, DMSO-d6), δ12.35 (s, 1H), 10.53 (s, 1H), 8.87 (s, 1H), 8.40–8.20 (m, 1H), 8.17 (d, J=8.8 Hz, 1H)7.61 (bs, 1H), 7.51 (bs, 1H), 5.67–5.55 (m, 2H), 5.23–5.18 , (m, 1H), 5.10 (d, J=12 Hz, 1H), 4.68–4.57 (m, 1H), 4.50 (bd, J=12 Hz, 1H), 4.46–4.37 (m, 1H), 4.07 (d, J=8.0 Hz, 1H), 3.95 (s, 3H), 3.17 (s, 3H), 2.78–2.58 (m, 1H), 2.42 (s, 2H), 2.29–2.19 (m, 1H), 2.19–2.09 (m, 1H), 1.71 (dd, J=7.8, 7.6 Hz, 1H), 1.67–1.55 (m, 4H), 1.55–1.37 (m, 4H), 1.04 (s, 9H), 0.98 (s, 9H), 0.97–0.87 (m, 2H). MS (electrospray): 896.5 (M+H)+, and 894.5 (M−H)−. RP-HPLC: Rt=6.7 minutes (homogeneity=100%).

Example 8

Preparation of Compound 107

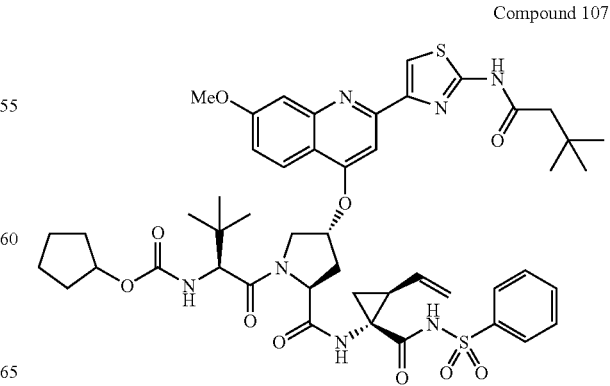

Compound 107

Using the same procedure described in Example 7 and using benzenesulfonamide instead of methylsulfonamide gave compound 107 as a pale yellow amorphous solid in 54% yield.

$^1$H NMR (DMSO-d6) δ12.39 (s, 1H), 10.89 (s, 1H), 8.83 (s, 1H), 8.40–8.22 (m, 1H), 8.18 (d, J=8.4 Hz, 1H), 7.90 (s, 1H), 7.88 (s, 1H), 7.67–7.63 (m, 1H), 7.63–7.54 (m, 3H), 7.54–7.45 (m, 1H), 7.30–7.15 (m, 1H), 7.10 (d, J=7.8 Hz, 1H), 5.62–5.51 (m, 1H), 5.38–5.26 (m, 1H), 5.16–5.08 (m, 1H), 4.93 (d, J=10.4 Hz, 1H), 4.70–4.58 (m, 1H), 4.57–4.49 (m, 1H), 4.48–4.39 (m, 1H), 4.09 (d, J=7.8 Hz, 1H), 3.95 (s, 3H), 2.69–2.59 (m, 1H), 2.41 (s, 2H), 2.28–2.16 (m, 1H), 2.14–2.04 (m, 1H), 1.72–1.52 (m, 4H), 1.51–1.37 (m, 4H), 1.29–1.22 (m, 1H), 1.03 (s, 9H), 1.00 (s, 9H), 0.99–0.92 (m, 1H). MS (electrospray); 958.5 (M+H)+, and 956.5 (M−H)−. RP-HPLC: Rt=7.2 minutes (homogeneity=95%).

Example 9

NS3-NS4A Protease Assay

The enzymatic assay used to evaluate the present compound is described in WO 00/09543 and WO 00/59929.

Example 10

Cell Based HCV RNA Replication Assay

Cell Culture

Huh7 cells that stably maintain a subgenomic HCV replicon were established as previously described (Lohman et al., 1999. Science 285:110–113) and designated as the S22.3 cell-line. S22.3 cells are maintained in Dulbecco's Modified Earle Medium (DMEM) supplemented with 10% FBS and 1 mg/mL neomycin (Standard Medium). During the assay, DMEM medium supplemented with 10% FBS, containing 0.5% DMSO and lacking neomycin was used (Assay Medium). 16 hours prior to compound addition, S22.3 cells are trypsinized and diluted to 50 000 cells/ml in Standard Medium. 200 μL (10 000 cells) are distributed into each well of a 96-well plate. The plate was then incubated at 37° with 5% CO$_2$ until the next day.

Reagents and Materials:

| Product | Company | Catalog # | Storage |
| --- | --- | --- | --- |
| DMEM | Wisent Inc. | 10013CV | 4° C. |
| DMSO | Sigma | D-2650 | RT |
| Dulbecco's PBS | Gibco-BRL | 14190-136 | RT |
| Fetal Bovine Serum | Bio-Whittaker | 14-901F | −20° C./4° C. |
| Neomycin (G418) | Gibco-BRL | 10131-027 | −20° C./4° C. |
| Trypsin-EDTA | Gibco-BRL | 25300-054 | −20° C./4° C. |
| 96-well plates | Costar | 3997 | RT |
| PVDF 0.22 μm Filter Unit | Millipore | SLGV025LS | RT |
| Deep-Well Titer Plate Polypropylene | Beckman | 267007 | RT |

Preparation of Test Compound

10 μL of test compound (in 100% DMSO) was added to 2 ml of Assay Medium for a final DMSO concentration of 0.5% and the solution was sonicated for 15 min and filtered through a 0.22 μM Millipore Filter Unit. 900 μl was transfered into row A of a Polypropylene Deep-Well Titer Plate. Rows B to H, contain 400 μL aliquots of Assay Medium (containing 0.5% DMSO), and are used to prepare serial dilutions (1/2) by transferring 400 μl from row to row (no compound was included in row H).

Application of Test Compound to Cells

Cell culture medium was aspirated from the 96-well plate containing the S22.3 cells. 175 μL of assay medium with the appropriate dilution of test compound was transferred from each well of the compound plate to the corresponding well of the cell culture plate (row H was used as the "No inhibition control"). The cell culture plate was incubated at 37° with 5% CO$_2$ for 72 h.

Extraction of Total Cellular RNA

Following the 72 h incubation period, the total cellular RNA was extracted from the S22.3 cells of the 96-well plate using the RNeasy 96 kit (Qiagen®, RNeasy Handbook. 1999.). Briefly, assay medium was completely removed from cells and 100 μL of RLT buffer (Qiagen®) containing 143 mM β-mercaptoethanol was added to each well of the 96-well cell-culture plate. The microplate was gently shaken for 20 sec. 100 μL of 70% ethanol was then added to each microplate well, and mixed by pipetting. The lysate was removed and applied to the wells of a RNeasy 96 (Qiagen®) plate that was placed on top of a Qiagen® Square-Well Block. The RNeasy 96 plate was sealed with tape and the Square-Well Block with the RNeasy 96 plate was loaded into the holder and placed in a rotor bucket of a 4K15C centrifuge. The sample was centrifuged at 6000 rpm (~5600×g) for 4 min at room temperature. The tape was removed from the plate and 0.8 ml of Buffer RW1 (Qiagen® RNeasy 96 kit) was added to each well of the RNeasy 96 plate. The RNeasy 96 plate was sealed with a new piece of tape and centrifuged at 6000 rpm for 4 min at room temperature. The RNeasy 96 plate was placed on top of another clean Square-Well Block, the tape removed and 0.8 ml of Buffer RPE (Qiagen® RNeasy 96 kit) was added to each well of the RNeasy 96 plate. The RNeasy 96 plate was sealed with a new piece of tape and centrifuged at 6000 rpm for 4 min at room temperature. The tape was removed and another 0.8 ml of Buffer RPE (Qiagen® RNeasy 96 kit) was added to each well of the RNeasy 96 plate. The RNeasy 96 plate was sealed with a new piece of tape and centrifuged at 6000 rpm for 10 min at room temperature. Tape was removed, the RNeasy 96 plate was placed on top of a rack containing 1.2-mL collection microtubes. The RNA was eluted by adding 50 μL of RNase-free water to each well, sealing plate with a new piece of tape and incubated for 1 min at room temperature. The plate was then centrifuged at 6000 rpm for 4 min at room temperature. The elution step was repeated with a second volume of 50 μl RNase-free water. The microtubes with total cellular RNA are stored at −70°.

Quantification of Total Cellular RNA

RNA was quantified on the STORM® system (Molecular Dynamics®) using the RiboGreen® RNA Quantification Kit (Molecular Probes®). Briefly, the RiboGreen reagent was diluted 200-fold in TE (10 mM Tris-HCl pH=7.5, 1 mM EDTA). Generally, 50 μL of reagent was diluted in 10 mL TE. A Standard Curve of ribosomal RNA was diluted in TE to 2 μg/mL and pre-determined amounts (100, 50, 40, 20, 10, 5, 2 and 0 μL) of the ribosomal RNA solution are then transferred in a new 96-well plate (COSTAR # 3997) and the volume was completed to 100 μL with TE. Generally, column 1 of the 96-well plate was used for the standard curve and the other wells are used for the RNA samples to be quantified. 10 μL of each RNA sample that was to be quantified, was transferred to the corresponding well of the 96-well plate and 90 μL of TE was added. One volume (100 μL) of diluted RiboGreen reagent was added to each well of the 96-well plate and incubated for 2 to 5 minutes at room temperature, protected from light (a 10 μL RNA sample in a 200 uL final volume generates a 20× dilution). The fluorescence intensity of each well was measured on the STORM® system (Molecular Dynamics®). A standard curve was created on the basis of the known quantities of the ribosomal RNA and the resulting fluorescent intensities. The RNA concentration in the experimental samples was determined from the standard curve and corrected for the 20× dilution.

Reagents and Materials:

| Product | Company | Catalog # | Storage |
|---|---|---|---|
| DEPC | Sigma | D5758 | 4° C. |
| EDTA | Sigma | E5134 | RT |
| Trizma-Base | Sigma | T8524 | RT |
| Trizma-HCl | Sigma | T7149 | RT |
| Collection Tube Strips | Qiagen | 19562 | RT |
| Ribogreen RNA Quantitation Kit | Molecular Probe | R11490 | −20° C. |
| Rneasy 96 Kit | Qiagen | 74183 | RT |
| Square-Well Blocks | Qiagen | 19573 | RT |

Real-Time RT-PCR

The Real-Time RT-PCR was performed on the ABI Prism 7700 Sequence Detection System using the TaqMan EZ RT-PCR Kit from (Perkin-Elmer Applied Biosystems®). RT-PCR was optimized for the quantification of the 5' IRES of HCV RNA by using the Taqman technology (Roche Molecular Diagnostics Systems) similar to the technique previously described (Martell et al., 1999. J. Clin. Microbiol. 37:327–332). The system exploits the 5'-3' nucleolytic activity of AmpliTaq DNA polymerase. Briefly, the method utilizes a dual-labeled fluorogenic hybridization probe (PUTR Probe) that specifically anneals to the template between the PCR primers (primers 8125 and 7028). The 5' end of the probe contains a fluorescent reporter (6-carboxyfluorescein [FAM]) and the 3' end contains a fluorescent quencher (6-carboxytetramethylrhodamine [TAMRA]). The FAM reporter's emission spectrum was suppressed by the quencher on the intact hybridization probe. Nuclease degradation of the hybridization probe releases the reporter, resulting in an increase in fluorescence emission. The ABI Prism 7700 sequence detector measures the increase in fluorescence emission continuously during the PCR amplification such that the amplified product was directly proportion to the signal. The amplification plot was analysed early in the reaction at a point that represents the logarithmic phase of product accumulation. A point representing a defined detection threshold of the increase in the fluorescent signal associated with the exponential growth of the PCR product for the sequence detector was defined as the cycle threshold ($C_T$). $C_T$ values are inversely proportional to the quantity of input HCV RNA; such that under identical PCR conditions, the larger the starting concentration of HCV RNA, the lower the $C_T$. A standard curve was created automatically by the ABI Prism 7700 detection system by plotting the $C_T$ against each standard dilution of known HCV RNA concentration.

Reference samples for the standard curve are included on each RT-PCR plate. HCV Replicon RNA was synthesized (by T7 transcription) in vitro, purified and quantified by $OD_{260}$. Considering that 1 μg of this RNA=$2.15 \times 10^{11}$ RNA copies, dilutions are made in order to have $10^8$, $10^7$, $10^6$, $10^5$, $10^4$, $10^3$ or $10_2$ genomic RNA copies/5 μL. Total cellular Huh-7 RNA was also incorporated with each dilution (50 ng/5 μL). 5 μL of each reference standard (HCV Replicon+ Huh-7 RNA) was combined with 45 μL of Reagent Mix, and used in the Real-Time RT-PCR reaction.

The Real-Time RT-PCR reaction was set-up for the experimental samples that were purified on RNeasy 96-well plates by combining 5 μl of each total cellular RNA sample with 45 μL of Reagent Mix.

Reagents and Materials:

| Product | COMPANY | Catalog # | Storage |
|---|---|---|---|
| TaqMan EZ RT-PCR Kit | PE Applied Biosystems | N808-0236 | −20° C. |
| MicroAmp Optical Caps | PE Applied Biosystems | N801-0935 | RT |
| MicroAmp Optical 96-Well Reaction Plate | PE Applied Biosystems | N801-0560 | RT |

Reagent Mix Preparation:

| Component | Volume for one sample (μL) | Volume for One Plate (μL) (91 samples + Dead Volume) | Final conc. |
|---|---|---|---|
| Rnase-free water | 16.5 | 1617 | |
| 5X TaqMan EZ buffer | 10 | 980 | 1X |
| $Mn(OAc)_2$ (25 mM) | 6 | 588 | 3 mM |
| dATP (10 mM) | 1.5 | 147 | 300 μM |
| dCTP (10 mM) | 1.5 | 147 | 300 μM |
| dGTP (10 mM) | 1.5 | 147 | 300 μM |
| dUTP (20 mM) | 1.5 | 147 | 600 μM |
| Forward Primer (10 μM) | 1 | 98 | 200 nM |
| Reverse Primer (10 μM) | 1 | 98 | 200 nM |
| PUTR probe (5 μM) | 2 | 196 | 200 nM |
| rTth DNA polymerase (2.5 U/μL) | 2 | 196 | 0.1 U/μL |
| AmpErase UNG (1 U/μL) | 0.5 | 49 | 0.01 U/μL |
| Total Volume | 45 | 4410 | |

```
Forward Primer Sequence (SEQ ID. 1): 5'- ACG CAG
AAA GCG TCT AGC CAT GGC GTT AGT - 3'

Reverse Primer Sequence (SEQ ID NO. 2): 5' - TCC
CGG GGC ACT CGC AAG CAC CCT ATC AGG - 3'

Note: Those primers amplify a region of 256-nt
present within the 5' untranslated region of HCV.

PUTR Probe Sequence (SEQ ID NO. 3): 6FAM  - TGG
TCT GCG GAA CCG GTG AGT ACA CC - TAMRA
```

No Template Controls (NTC): On each plate, 4 wells are used as "NTC". For these controls, 5 μl of water are added to the well in place of RNA.

Thermal Cycling Conditions:

| | |
|---|---|
| 50° C. | 2 min |
| 60° C. | 30 min |
| 95° C. | 5 min |
| 95° C. | 15 sec } for 2 cycles |
| 60° C. | 1 min |
| 90° C. | 15 sec } for 40 cycles |
| 60° C. | 1 min |

Following the termination of the RT-PCR reaction the data analysis requires setting of threshold fluorescence signal for the PCR plate and a standard curve was constructed by plotting the Ct value versus RNA copy number used in each reference reaction. The Ct values obtained for the assay samples are used to interpolate an RNA copy number based on the standard curve.

Finally, the RNA copy number was normalized (based on the RiboGreen RNA quantification of the total RNA extracted from the cell culture well) and expressed as genome equivalents/μg of total RNA [ge/μg].

The RNA copy number [g.e./μg] from each well of the cell culture plate was a measure of the amount of replicating HCV RNA in the presence of various concentrations of inhibitor. The % inhibition was calculated with the following equation:

$$100-[(g.e./\mu g\ inh)/(g.e./\mu g\ ctl)\times 100].$$

A non-linear curve fit with the Hill model was applied to the inhibition-concentration data, and the 50% effective concentration ($EC_{50}$) was calculated by the use of SAS software (Statistical Software System; SAS Institute, Inc. Cary, N.C.).

When the compounds of this invention were evaluated in the preceding enzymatic and cell based assays, the compounds were found to be highly active. More specifically, the compounds had $IC_{50}$'s below 0.1 μM in the NS3-NS4A protease assay, and $EC_{50}$'s below 0.5 μM in the cell based HCV RNA replication assay.

Example 11

Specificity Assays

The specificity assays used to evaluate the selectivity of this compound are described in WO 00/09543.

When the compounds were evaluated in the specifity assays, the compounds of formula 1 were found to be selective in that they do not show significant inhibition in the Human Leukocyte Elastase and Cathepsin B assays.

Example 12

Pharmacokinetic Properties

The present compounds also show good pharmacokinetic properties such as detectable plasma levels in the rat at 1 hour and 2 h after an oral dose of 4 or 5 mg/kg. More explicitly, the following assay, an in vivo oral absorption screen, was used to determine plasma levels of test compounds in a rat after oral administration:

Materials and Methods:

1. Method Used to Pool Compounds ("Cassette Selection"):

The selection of compounds to be pooled into a "cassette" was based on their structural similarity and physicochemical properties. A solid phase extraction method applicable to all the selected compounds was established. Based on the initial testing where each compound was spiked into rat plasma and run through HPLC or HPLC/MS at a concentration of 0.5 μM, the retention time, ionic mass, and the possible separation among compounds by HPLC and/or HPLC/MS were used as basis for pooling 3-4 compounds into one "cassette".

2. Oral Vehicle and Compound Preparation:

Each "cassette" contains 3-4 compounds at 5 or 4 mg/kg for each compound. The cassettes were prepared as an oral suspension in 0.5% aqueous methylcellulose and 0.3% of polyoxyethylene (20) sorbiton monooleate (Tween-80). The dosing volume was 10 ml/kg via oral gavage.

3. Dosing and Plasma Sampling:

Male Sprague Dawley rats were fasted overnight in individual cages, with access to aqueous 10% dextrose. Two rats were dosed with each "cassette". Plasma samples (~1 ml) were collected at 1 and 2 h post-dosing from the 2 rats and pooled for extraction and analysis.

4. Compound Extraction and Analysis:

From each cassette, plasma samples at 1 and 2 h, blank plasma, blank plasma, spiked with all the compounds at 0.5 μM of each, are extracted by the solid phase extraction method. Samples were analyzed by HPLC and HPLC/MS for comparison purpose. Plasma concentrations are estimated based on the single concentration of 0.5 μM standard.

RESULTS

When assayed in the preceding screen the compounds of examples 1 to 8 of this invention were found to present in significant levels in the plasma at the 1 hour and 2 hour intervals following oral administration, averaging blood plasma levels of 0.83 μM and 0.75 μM respectively.

This demonstration of in vivo oral absorption for the tripeptide compounds of this invention in noteworthy, in view of the poor oral absortion generally attributed to this class of peptides. The ready oral absorption renders the compounds useful for treating of HCV infection.

What is claimed is:

1. A compound of formula (I):

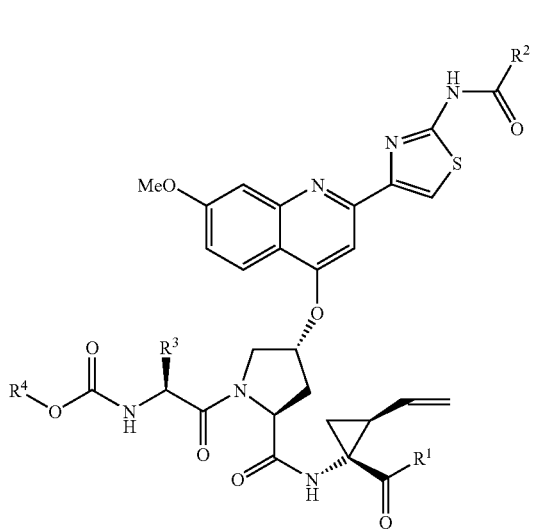

(I)

wherein $R^1$ is hydroxy or $NHSO_2R^{14}$ wherein $R^{14}$ is $(C_{1-8})$ alkyl, $(C_{3-7})$cycloalkyl or $\{(C_{1-6})alkyl\text{-}(C_{3-7})cycloalkyl\}$, which are all optionally substituted from 1 to 3 times with halo, cyano, nitro, O—$(C_{1-6})$alkyl, amido, amino or phenyl, or $R^{14}$ is $C_6$ or $C_{10}$ aryl which is optionally substituted from 1 to 3 times with halo, cyano, nitro, $(C_{1-6})$alkyl, O—$(C_{1-6})$ alkyl, amido, amino or phenyl; $R^2$ is t-butyl, —$CH_2$—C($CH_3$)$_3$, or —$CH_2$-cyclopentyl; $R^3$ is t-butyl or cyclohexyl and $R^4$ is cyclobutyl, cyclopentyl, or cyclohexyl; or a pharmaceutically acceptable salt thereof.

2. The compound of formula I according to claim 1, wherein $R^1$ is hydroxy, $NHSO_2Me$, $NHSO_2$-cyclopropyl, or $NHSO_2Ph$.

3. The compound of formula I according to claim 2, wherein $R^1$ is $NHSO_2Me$ or hydroxy.

4. The compound of formula I according to claim 3, wherein $R^1$ is hydroxy.

5. The compound of formula I according to claim 1, wherein $R^2$ is t-butyl or $CH_2$—C($CH_3$)$_3$.

6. The compound of formula I according to claim 5, wherein $R_2$ is $CH_2$—C($CH_3$)$_3$.

7. The compound of formula I according to claim 1, wherein $R^3$ is t-butyl.

8. The compound of formula I according claim 1, wherein $R^4$ is cyclopentyl or cyclohexyl.

9. The compound of formula I according to claim 8, wherein $R^4$ is cyclopentyl.

10. The compound of formula I as defined in claim 1, wherein $R^1$ is hydroxy, $R^2$ is $CH_2$—C($CH_3$)$_3$, $R^3$ is t-butyl and $R^4$ is cyclopentyl.

11. The compound of formula I as defined in claim 1, wherein $R^1$ is hydroxy, $R^2$ and $R^3$ each is t-butyl and $R^4$ is cyclopentyl.

12. The compound of formula I as defined in claim 1, wherein $R^1$ is hydroxy, $R^2$ is $CH_2$—C($CH_3$)$_3$, $R^3$ is cyclohexyl and $R^4$ is cyclopentyl.

13. The compound of formula I as defined in claim 1, wherein $R^1$ is hydroxy, $R^2$ is $CH_2$—C($CH_3$)$_3$, and $R^3$ and $R^4$ each is cyclohexyl.

14. The compound of formula I as defined in claim 1, wherein $R^1$ is hydroxy, $R^2$ is cyclopentylmethyl, $R^3$ is t-butyl, and $R^4$ is cyclobutyl.

15. The compound of formula I as defined in claim 1, wherein $R^1$ is hydroxy, $R^2$ is $CH_2$—C($CH_3$)$_3$, $R^3$ is t-butyl and $R^4$ is cyclobutyl.

16. The compound of formula I as defined in claim 1, wherein $R^1$ is $NHSO_2Me$, $R^2$ is $CH_2$—C($CH_3$)$_3$ $R^3$ is t-butyl and $R^4$ is cyclopentyl.

17. The compound of formula I as defined in claim 1, wherein $R^1$ is $NHSO_2Ph$, $R^2$ is $CH_2$—C($CH_3$)$_3$, $R^3$ is t-butyl and $R^4$ is cyclopentyl.

18. A pharmaceutical composition comprising an anti-hepatitis C virally effective amount of a compound of formula I according to claim 1, or a pharmaceutically acceptable salt thereof, in admixture with one or more pharmaceutically acceptable carriers, adjuvants or vehicles.

19. The pharmaceutical composition according to claim 18, further comprising one or more other anti-HCV agents.

20. The pharmaceutical composition according to claim 19, wherein at least one of the other anti-HCV agents is selected from: α-interferon or pegylated α-interferon.

21. The pharmaceutical composition according to claim 19, wherein at least one of the other anti-HCV agents is ribavirin.

22. The pharmaceutical composition according to claim 19, wherein at least one of the other anti-HCV agents is an inhibitor of HCV polymerase.

23. The pharmaceutical composition according to claim 19, wherein at least one of the other anti-HCV agents is selected from inhibitors of: helicase, NS2/3 protease and internal ribosome entry site (IRES).

24. A method for treating a hepatitis C viral infection in a mammal comprising administering to the mammal an anti-hepatitis C virally effective amount of a compound of formula I according to claim 1, or a pharmaceutically acceptable salt thereof.

25. A method for treating a hepatitis C viral infection in a mammal comprising administering to the mammal an anti-hepatitis C virally effective amount of the composition according claim 18.

26. A method for treating a hepatitis C viral infection in a mammal comprising administering to the mammal an anti-hepatitis C virally effective amount of the composition according claim 19.

27. A method for treating a hepatitis C viral infection in a mammal comprising administering to the mammal an anti-hepatitis C virally effective amount of a combination of the compound of formula I according to claim 1, or a pharmaceutically acceptable salt thereof, and one or more other anti-HCV agents, wherein said one or more other anti-HCV agents are administered prior to, concurrently with, or following the administration of the compound of formula I according to claim 1, or a pharmaceutically acceptable salt thereof.

28. The method according to claim 27, wherein at least one of the other anti-HCV agents is selected from: α-interferon or pegylated α-interferon.

29. The method according to claim 27, wherein at least one of the other anti-HCV agents is ribavirin.

30. The method according to claim 28, wherein at least one of the other anti-HCV agents is ribavirin.

31. The method according to claim 27, wherein at least one of the other anti-HCV agents is an inhibitor of HCV polymerase.

32. The method according to claim 27, wherein at least one of the other anti-HCV agents is selected from inhibitors of: helicase, NS2/3 protease and internal ribosome entry site (IRES).

33. The method according to claim 28, wherein at least one of the other anti-HCV agents is selected from inhibitors of: helicase, NS2/3 protease and internal ribosome entry site (IRES).

34. The method according to claim 29, wherein at least one of the other anti-HCV agents is selected from inhibitors of: helicase, NS2/3 protease and internal ribosome entry site (IRES).

35. The method according to claim 30, wherein at least one of the other anti-HCV agents is selected from inhibitors of: helicase, NS2/3 protease and internal ribosome entry site (IRES).

* * * * *